United States Patent [19]

Hudrlik

[11] Patent Number: 5,282,840
[45] Date of Patent: Feb. 1, 1994

[54] MULTIPLE FREQUENCY IMPEDANCE MEASUREMENT SYSTEM

[75] Inventor: Terrence R. Hudrlik, Fridley, Minn.

[73] Assignee: Medtronic, Inc., Minneapolis, Minn.

[21] Appl. No.: 857,896

[22] Filed: Mar. 26, 1992

[51] Int. Cl.⁵ ............................................. A61N 1/362
[52] U.S. Cl. ......................................... 607/28; 607/6; 128/734
[58] Field of Search ................... 128/734, 419 PG

[56] References Cited

U.S. PATENT DOCUMENTS

| | | | |
|---|---|---|---|
| 3,593,718 | 7/1971 | Krasner | 128/419 P |
| 4,223,678 | 9/1980 | Langer | 128/419 D |
| 4,596,251 | 6/1986 | Plicchi | 128/419 PG |
| 4,702,253 | 10/1987 | Nappholz | 128/419 PG |
| 4,757,815 | 6/1988 | Strandberg | 128/419 PG |
| 4,793,362 | 12/1988 | Tedner | 128/734 |
| 4,805,621 | 2/1989 | Heinze | 128/419 PG |
| 4,840,182 | 6/1989 | Carlson | 128/734 |
| 4,919,136 | 4/1990 | Alt | 128/419 P |
| 5,027,813 | 7/1991 | Pederson et al. | 128/734 |
| 5,080,586 | 1/1992 | Kawai | 128/734 |

OTHER PUBLICATIONS

Bioelectric Amplifiers in *Introduction to Biomedical Equipment Technology*, by Carr and Brown, John Wiley & Sons, 1981, pp. 41–44.

*Primary Examiner*—William E. Kamm
*Assistant Examiner*—Scott M. Getzow
*Attorney, Agent, or Firm*—Reed A. Duthler; Harold R. Patton

[57] ABSTRACT

A physiological monitoring system for monitoring the condition of a patient's body tissue. The device includes electrodes for contacting the tissue to be monitored, circuitry for generating electrical signals at at least two frequencies for application to the tissue and circuitry for monitoring the impedance of the tissue, at the frequencies applied. The device includes in addition apparatus for detecting changes in the relationship of the measured impedances at the frequencies applied, and for processing the detected changes in impedance relationship to provide an indication of the condition of the tissue. The monitoring apparatus may be practiced in the context of an implantable stimulator, such as a cardiac pacemaker, in which the pulse frequency is varied as a function of the detected condition of the tissue.

23 Claims, 4 Drawing Sheets

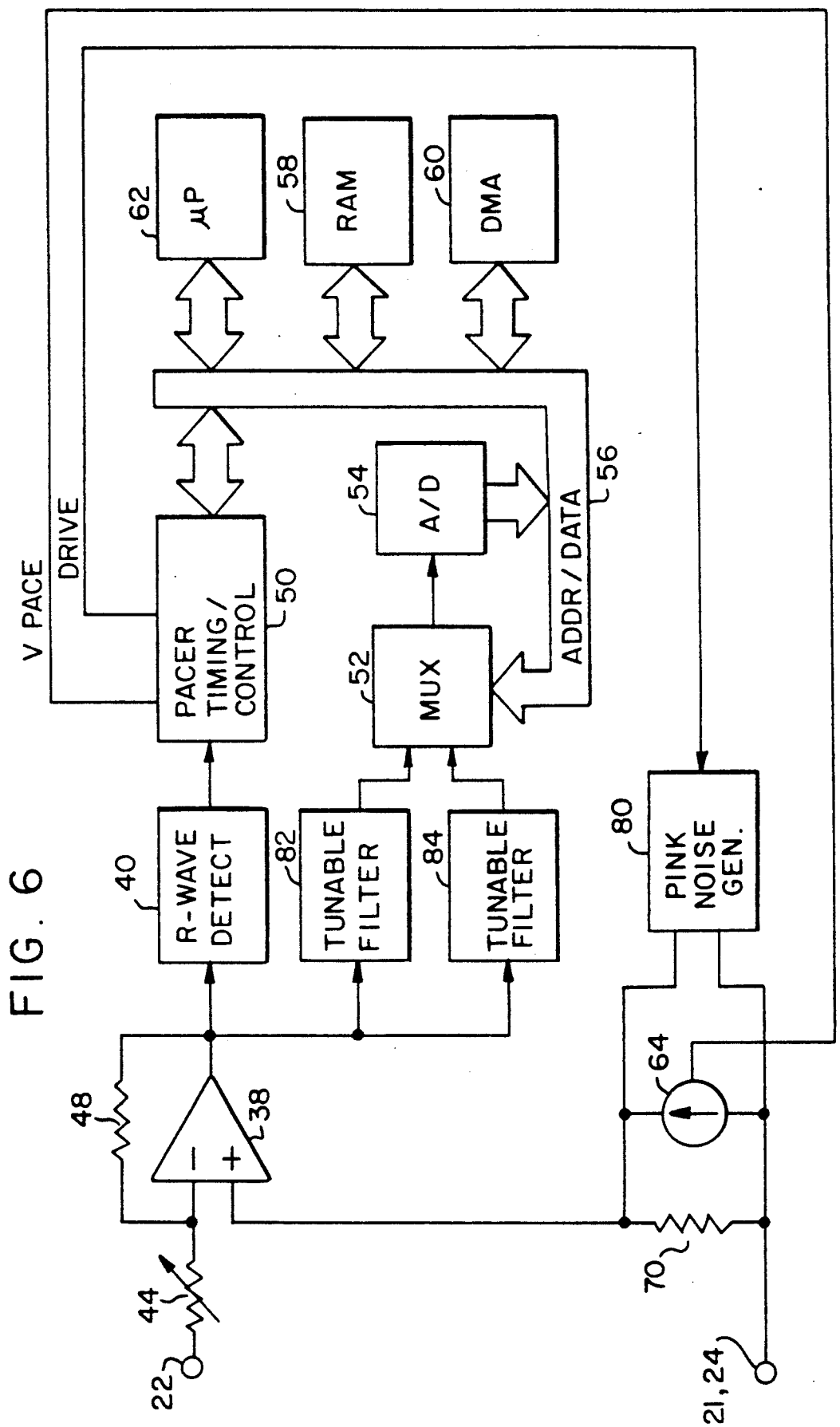

MULTIPLE FREQUENCY IMPEDANCE MEASUREMENT SYSTEM

CROSS-REFERENCED RELATED APPLICATIONS

Attention is drawn to the commonly assigned co-pending U.S. patent application Ser. No. 07/566,636, now abandoned, for a "Field Density Clamp for sensing Cardiac Depolarizations", filed Aug. 10, 1990 in the name of Terrence R. Hudrlik, U.S. patent application Ser. No. 07/626,061, now U.S. Pat. No. 5,156,149, for "Electronic Capture Detection for a Pacer", filed Dec. 12, 1990 and U.S. patent application Ser. No. 07/730,160, now U.S. Pat. No. 5,233,985, for a "Medical Stimulator With Operational Amplifier Output circuit", filed Jul. 15, 1991 in the name of Terrence R. Hudrlik, all three of which are incorporated herein by reference in their entireties. The present application is a continuation-in-part of all three of these cited applications.

BACKGROUND OF THE INVENTION

This invention relates to diagnostic and tissue stimulation devices such as implantable pacemakers, cardioverters and defibrillators, implantable monitoring devices and implantable drug dispensers, and more particularly to rate-responsive implantable pacemakers that vary their pacing rate as a function of the patient's metabolic demand for oxygenated blood.

Early pacemakers provided a fixed rate stimulation pulse generator that could be reset on demand by sensed atrial and/or ventricular depolarizations. Modern pacemakers include complex stimulation pulse generators, sense amplifiers and leads which can be configured or programmed to operate in single or dual chamber modes of operations, delivering pacing stimuli to the atrium and/or ventricle at fixed rates or rates that vary between an upper rate limit and a lower rate limit.

More recently, single and dual chamber pacemakers have been developed that respond to physiologic sensors which, with greater or lesser degrees of specificity, sense the body's need to deliver more or less oxygenated blood to the cardiovascular system. For example, rate responsive pacing systems have been developed and marketed which rely upon the patient's rate of respiration. Such pacemakers are described, for example, in U.S. Pat. Nos. 3,593,718 and 4,596,251 and have been commercialized by Biotec and Telectronics. These pacemakers use an impedance pneumograph for acquiring a respiration signal. More recently, it has been proposed to employ the variation and the amplitude of the peak-to-peak ECG signals as a rate control signal on the premise that the amplitude varies as a function of the patient's activity and/or respiration as disclosed in U.S. Pat. No. 4,757,815.

The impedance pneumograph measurement technique of the prior art involves the injection of a pulse or pulse burst of alternating current at subthreshold stimulation energy levels across a pair of electrodes and measuring voltage or current levels to derive an impedance measurement. The electrodes may be located one on either side of the chest, as in U.S. Pat. No. 4,596,251, issued to Plicchi, et al., both located in the heart as in U.S. Pat. No. 4,919,136, issued to Alt, or one electrode may be located in contact with the heart and one in the chest. U.S. Pat. No. 4,702,253 describes a system employing bipolar pacing electrodes. A constant voltage pulse train is injected into the tissue between one electrode and the pacemaker can and a measurement of the current taken between the other electrode in the heart and the pacemaker can. The impedance varies with exhalation and inhalation.

U.S. Pat. No. 4,805,621, issued to Heinze et al. suggests an approach to minimizing the effects of long term changes in overall tissue impedance on the accuracy of such systems. In the Heinze et al. device, the drive signal, as modulated by the tissue impedance is passed through a first low pass filter to strip off the drive signal frequency and produce a signal indicative of impedance variation over time, stated to correspond to respiratory activity. This impedance signal is then passed through a high pass filter to strip off the extremely low frequencies at which overall changes in tissue impedance are stated to occur.

SUMMARY OF THE INVENTION

In the study of the nature of the tissue-electrode interface and, in particular, in developing the theoretical basis for the operation of the field density clamp as set forth in U.S. patent application Ser. No. 07/566,636, the inventor has explored the frequency dependant impedance characteristics of body tissue. If the wide band impedance is measured across two electrodes in contact with body tissue and displayed in a Cole-Cole plot, the impedance plot or impedance "signature" typically displays several peaks and valleys. The frequencies associated with the peaks are referred to in the literature as "turnover frequencies".

The inventor has determined that gross tissue insults, such as significant reduction of blood supply to the tissue, causes a dramatic shift in the impedance signature. It is expected that this type of change will also occur as a result of gradually developed ischemic conditions. It is also expected that in some cases, where the tissue is not permanently damaged, the original signature will return when blood flow is restored.

The inventor has also noted that different tissues may have impedance peaks at substantially different frequencies. A measurement of impedance and frequency across two spaced electrodes will reflect several impedance peaks depending on the tissue types within the sensing field of the electrodes. There will be corresponding impedance minimums between the peaks. The impedance signatures indicate that the tissues adjacent and between the electrodes can be modeled as a series of parallel R-C blocks. Different tissue types, with different impedance peaks, would correspondingly be modeled as series of R-C blocks having different component values.

The present invention takes advantage of this physiological phenomenon to provide an impedance sensing system which may be optimized to sense impedance variations associated with one or more desired tissue types. The present invention is also believed to provide an increased signal to noise ratio with regard to sensing of impedance modulations of each tissue type. The present invention employs multiple, spectrally selected excitation signals to accomplish these results.

It is proposed in the present invention that electrodes be used to apply a plurality of spectrally selected excitation signals simultaneously or sequentially over a period of time. The measured impedances at the selected frequencies may be used either to sense the condition of the tissue to which the excitation signals are applied or to sense other physiologic parameters related to the impedance of the tissue. Two or more excitation frequencies are typically used, one at an impedance peak, one displaced from the impedance peak, preferably at a frequency which defines an impedance minimum. The excitation frequencies should be chosen such that the event of interest causes a substantial change in the relative values in the impedances at the excitation frequencies.

For example, multiple frequency excitation signals may be used to detect cardiac tissue distress, such as ischemia or the response of the tissue to drug treatment. Multiple frequency excitation signals may be alternatively be used to measure respiration characteristics or other parameters related to the level of the patient's activity. In conjunction with this aspect of the invention, the invention may provide a heart pacemaker which varies the pacing rate in dependence upon the impedance measurements.

The invention is preferably practiced using an operational amplifier input/output circuit as described in the above cited application Ser. No. 07/730,160. The amplifier may be used both to provide the drive or excitation signal and measure the impedance of the body tissue in question, allowing the use of a two electrode system The amplifier may also be used to pace the heart and to sense depolarizations of heart tissue, in those embodiments taking the form of cardiac pacemakers.

BRIEF DESCRIPTION OF THE DRAWINGS

The above and still further objects, features and advantages of the present invention will become apparent from the following detailed description of a presently preferred embodiment, taken in conjunction with the accompanying drawings.

FIG. 6 is a block diagram of an alternative embodiment of the present invention.

DETAILED DESCRIPTION OF THE PREFERRED EMBODIMENT

In the following description, reference is made to an illustrative embodiment for carrying out the invention. It is understood that other embodiments may be utilized without departing from the scope of the invention.

In accordance with the present invention, a technique is employed to provide time varying signals that contain information regarding the short or long term modulation of the inter-electrode tissue impedance properties by physical movement, such as respiration or patient activity, and/or the changes related to the modulation of the tissue impedance due to myocardial depolarizations, ischemia, allograft rejection, drug therapy or other causes. It should also be noted that the characteristic impedance of the lead body may vary as a result of fracture of the lead conductors or insulation degradation. The impedance measurement system disclosed herein may also be used to identify such conditions.

Figure 1:
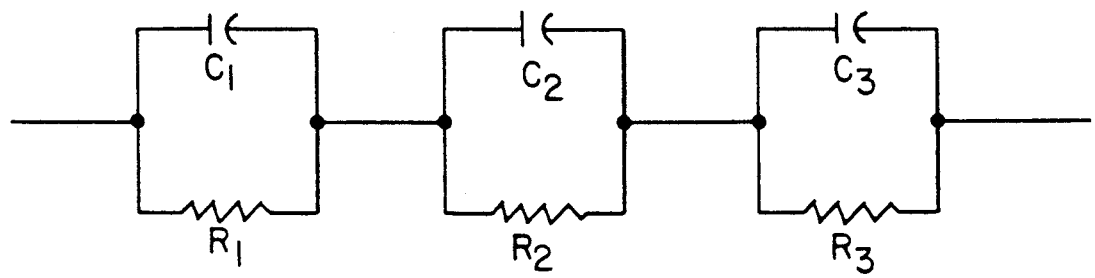
FIG. 1 is an illustration of a circuit simulating the various source impedances of several tissue types, within the field of the electrodes used to apply excitation signals.

As stated above, different tissue types have different frequency sensitive impedance characteristics that may be modeled by a series of parallel resistance and capacitive elements denoted $Z_1$, $Z_2$ and $Z_3$ in the illustration of FIG. 1. Each of these impedance elements has a different time constant, and the local impedance peak of each one of the elements is referred to herein as the "turnover frequency" in the literature.

It has also been previously noted by the inventor that the frequency position of these turnover frequency peaks are very sensitive to tissue condition, ischemia being specifically studied. The tracking of these impedance peaks over time provides information regarding changes in tissue condition. Similarly, the tracking of these peaks on an hourly basis in a patient on a drug regimen for treating cardiac disease may provide an indication of the effectiveness of the drug's therapy.

Use of two spectrally selected excitation signals to "focus" in on and specifically tune in at two frequencies would provide two views of the same tissue from slightly different aspects. In addition, when these frequencies are set at local minima and maxima, the change in impedance due to the occurrence of the event of interest will be significantly different for the two frequencies. The relative difference between the impedance changes at the selected frequencies can be used to provide a self-normalizing ratio, based on the individual in whom the device is implanted, which can be used to identify the occurrence of the event.

The selected excitation frequencies are preferably separated by at least a factor of 10. This separation factor readily allows tuned filter separation of the applied signals as modulated by the impedance of the tissue. As digital filtration techniques improve with time, it is expected that the separation factor may be substantially reduced. The spectrally selected excitation signals may be applied sequentially in time multiplexed fashion or may be applied simultaneously between electrodes coupled to the tissue to be measured.

In those embodiments in which the invention takes the form of a cardiac pacemaker, the excitation signals may be applied between the probe and can electrodes or between the probe electrode and a second electrode on or in the heart. In embodiments in which the impedance measurement system is used to detect basal conductance changes or to analyze myocardial depolarizations, the excitation signals are preferably applied during defined time intervals closely following delivery of pacing pulses or detection of the occurrence of depolarizations. In other embodiments, including embodiments directed toward assessing the impact of drug therapies, other measurement times may be more optimal.

Figure 2:
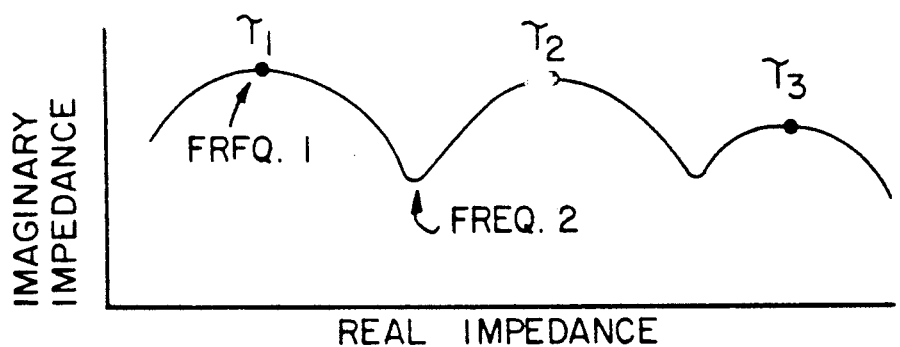
FIG. 2 illustrates the impedance between the electrodes used to apply excitation signals to body tissue as a function of the frequency of the excitation signals.

FIG. 2 is a Cole-Cole plot of real versus imaginary impedance, taken across a band of frequencies. In accordance with the present invention, it is contemplated that the spectrally selected excitation signal may include a first drive frequency signal (F1) tuned to a turnover frequency (a local maximum) and a second drive frequency signal (F2) tuned to a frequency corresponding to a local minimum of the impedance plot set forth in FIG. 2. In this fashion, two views of the same tissue from slightly different aspects may be obtained. Similarly, if two tissue types are to be monitored, three or more frequencies may be employed, with each tissue type having an associated pair of frequencies particularly adapted to reflect changes in that tissue's condition.

The increased signal to noise (S/N) ratio provided by the two views provides isolation of the electrokinetic disturbance, noise caused dy electrode and/or tissue movement at their interface. In embodiments directed toward respiration monitoring, the electrodes are mounted such that a significant portion of lung tissue is between the electrodes. The result is impedance measurement that modulate with a high degree of correlation to respiration or activity. In embodiments directed toward detection of cardiac ischemia, at least one of the electrodes is located adjacent heart tissue.

An increased S/N ratio compared to single frequency systems is realized due to the fact that long term changes in overall tissue/electrode impedance generally result in moving the impedance plot illustrated in FIG. 2 upward or downward, so the relative impedance difference between the two chosen frequencies is not greatly affected. By using the relative amplitudes of the measured impedance at the selected turnover point as compared to the measured impedance at the selected second frequency, the effects of changes in overall tissue/electrode impedance are minimized. Thus, the present invention provides a new and unobvious method of dealing with this problem in a fashion unrelated to that suggested in the above-cited Heinze et al. U.S. Pat. No. 4,805,621.

Figure 3:
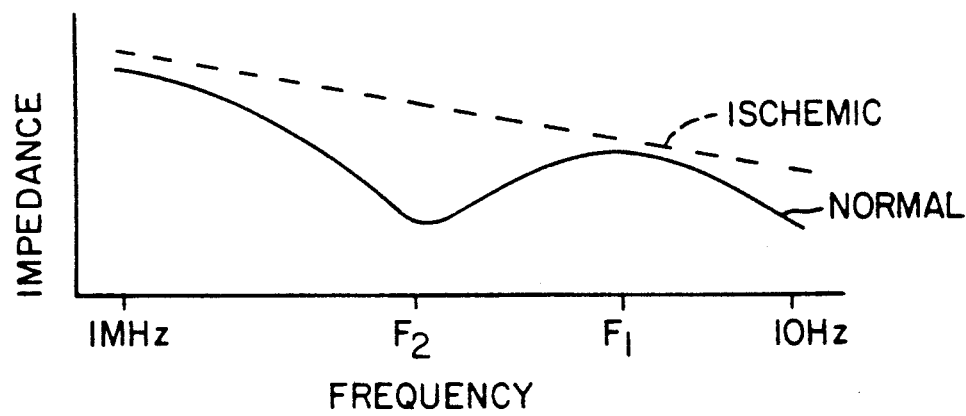
FIG. 3 is a graphical depiction of the effect of ischemia on the impedance versus frequency curve illustrated in FIG. 2.

FIG. 3 illustrates a simulated plot of frequency versus impedance taken across normal and ischemic intestinal tissue, using sinusoidal excitation signals. As illustrated, normal tissue displays a local impedance peak at frequency F-1 and a local impedance minimum at a frequency F-2. Ischemic tissue, on the other hand, displays a substantially different frequency plot. In general, changes in tissue condition, for example due to ischemia or drug therapy may be reflected by a change in frequency dependent impedance characteristics. For example, the frequencies at which local, minima and maxima of impedance occur may be substantially shifted or rearranged, as illustrated in FIG. 3. Therefore, by monitoring the impedance characteristics across a plurality of frequencies, such changes can be discerned.

The frequency dependant impedance characteristics as illustrated in FIGS. 2 and 3 are believed to occur generally in body tissues, although the frequencies at which local maximums and minimums in the impedance plot will vary. Local impedance maximums and minimums may be determined empirically for the body tissue coupled to the electrodes. Given that such measurements may be readily accomplished with available apparatus, it is believed within the capabilities of one of skill in the art to measure and derive impedance plots as illustrated in FIGS. 2 and 3 for any particular electrode—tissue system.

In the context of FIG. 3, ischemia could be detected by placing electrodes on or in the tissue to be monitored or placing the tissue between the electrodes, and generating drive or excitation signals at frequencies at F-1 and F-2. By monitoring the relative impedance levels at frequencies F-1 and F-2, changes in the frequency dependent impedance characteristics of the tissue can readily be discerned. By selecting excitation signals associated with a local impedance maximum and a local impedance minimum, a shift in the frequencies of the minimum and the maximum may be readily detected due to their substantial effect on the relative impedance values at the two chosen frequencies.

For purposes of monitoring tissue impedance to ascertain changes in tissue condition, the measured impedance amplitudes can be averaged over extended periods of time, for example in the range of days to weeks, so that short term modulation of impedance characteristics of the tissue being monitored due to physical movement, respiration, peristaltic motion, etc. can be disregarded. Alternatively, short term modulation of the relationship between the impedances measured at the two frequencies due to the normal functioning of the tissue (e.g. modulation due to respiration or heartbeats) may be measured and recorded. Changes in the modulation amplitude and rate associated with such tissue-related activities may be measured and similarly be used to detect short or long term changes in tissue condition or overall metabolic functioning.

For example, short term changes in the measured modulation of the relationship of the impedances at the two frequencies due to heartbeats or respiration may be used to control the pacing rate of a cardiac pacemaker. Alternatively, longer term changes in the average modulation characteristics associated with heart contractions may be indicative of cardiac ischemia or other factor related to the condition of the heart tissue.

Figure 4A:
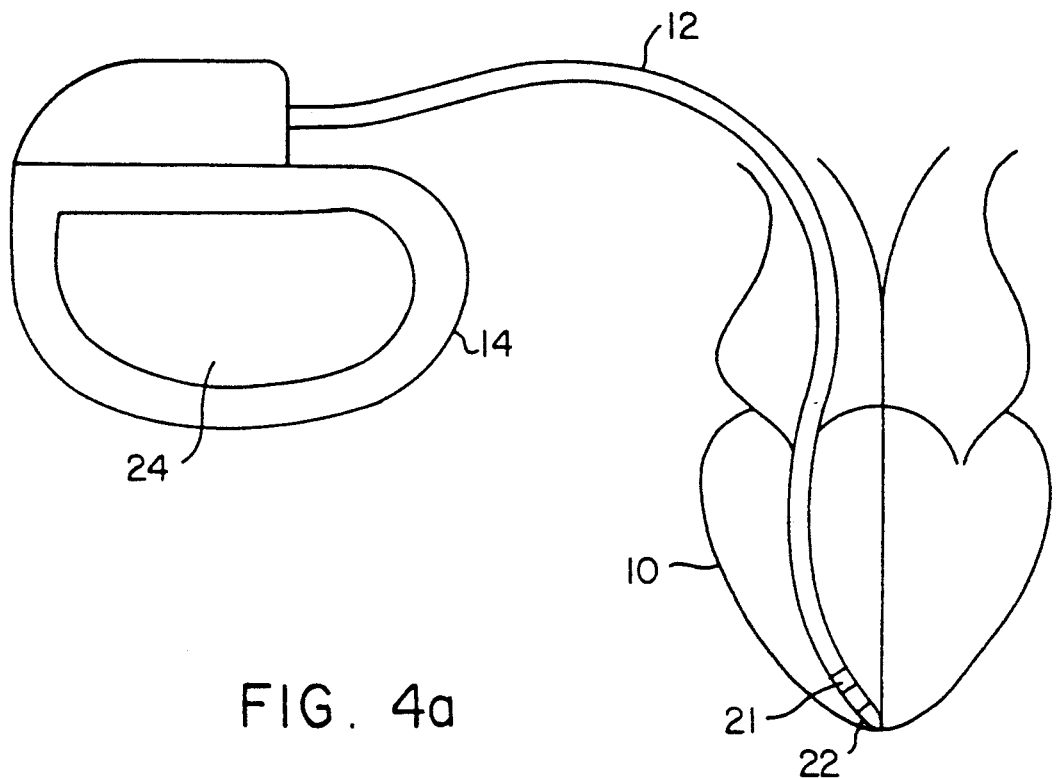
FIG. 4a is a schematic diagram depicting the interconnection between a pacer and the heart.

FIG. 4a is a drawing depicting the interconnection between a cardiac pacer and the heart. For purposes of illustration, a composite unipolar/bipolar ventricular inhibited pacer is shown with a lead bearing two electrodes situated in the ventricle. Typically, the pacemaker 14 is implanted beneath the skin, outside the rib-cage. A pacing lead 12 is passed transvenously into the right ventricle of the heart 10. The pacing lead 12 is used for supplying pacing pulses to the heart and for conducting electrical signals resulting from the depolarization of the heart to the pacemaker 14. Traditionally, there are two basic electrical configurations for pacing leads. A unipolar configuration would include tip electrode 22 and a can or case electrode 24. In a bipolar configuration, ring electrode 21 is used with tip electrode 22. Electrode 22, in direct contact with cardiac tissue is referred to herein as the "probe" electrode.

In unipolar configurations the implanted pacer is implanted with the can electrode surface 24 disposed toward the ribs 18 and generally toward the heart 10. This electrode configuration places at least the tip electrode 22 within the heart, and the case electrode 24 proximate the outside of the heart, with the syncytium of the heart and a significant amount of lung tissue located between the electrode poles. Typically, the distance between the distal tip electrode 22 and the pacer can electrode 24 is between 10 and 30 cm.

In bipolar configurations, the case electrode 24 is not used and the tip and proximal ring electrodes 22 and 21 are connected to the pacemaker pulse generator output circuit and sense amplifiers. Typically, the tip and ring electrodes 22 and 21 are spaced apart between 0.5 and 3.0 cm. In dual chamber pacemakers, unipolar and/or bipolar electrodes are similarly situated in or on the atrium or coronary sinus.

More recent pacemaker models often have the flexibility to employ combinations of unipolar and bipolar electrode configurations, under control of external programming commands. For example, unipolar pacing might be selected in conjunction with bipolar sensing. The present invention, if embodied as a pacemaker may employ any of the various unipolar and bipolar electrode configurations and combinations thereof Similarly, any two of the electrodes may be employed to deliver the excitation signals and to measure the tissue impedance.

Figures 4B, 4C, 4D:
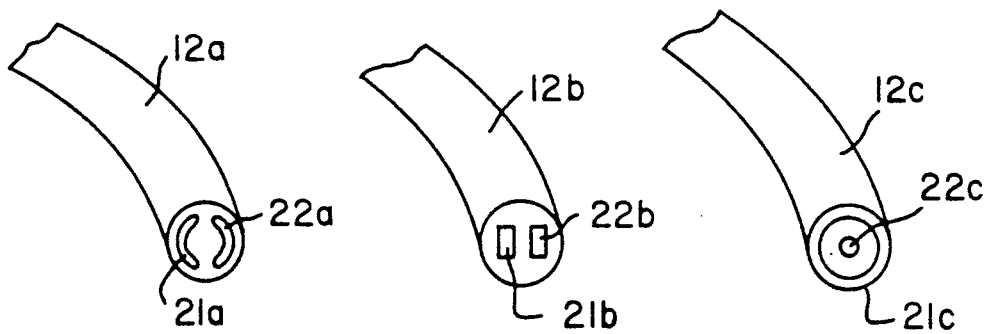
FIGS. 4b, 4c and 4d are drawings of possible electrode configurations for use in conjunction with the present invention.

FIGS. 4b, 4c and 4d illustrate alternative electrode configurations for use in conjunction with the present invention. The location of the electrodes will of course depend on the tissue being monitored, but in the context of measurement of heart tissue impedance, it is believed to locate both electrodes so that they directly contact heart tissue. The illustrated electrode configurations are intended for use in applying the excitation signals to the heart tissue and for measuring the impedance of the heart tissue, but may be valuable in measuring other tissue as well.

All three embodiments employ a pair of closely spaced electrodes mounted to the distal end of the lead body (12a, 12b, 12c). Electrodes 21a and 22a (FIG. 4b) take the form of a split ring. Electrodes 21b and 22b (FIG. 4c) are a pair of closely spaced rectangular electrodes. Electrodes 21c and 22c (FIG. 4d) include a ring electrode surrounding a small. central electrode. The electrodes of FIGS. 4b, 4c and 4d may also be used for R-wave sensing and cardiac pacing functions, either paired with one another or paired with other electrodes located on the lead body or on the pacer housing.

If the invention is embodied in the form of device which monitors other tissue types, other electrode configurations may be required, such electrodes mounted on separate leads, individually mounted to or inserted in the tissue to be monitored. For example, existing intramuscular electrodes, nerve stimulation electrodes and so forth or modified versions thereof may be employed.

Figure 5:
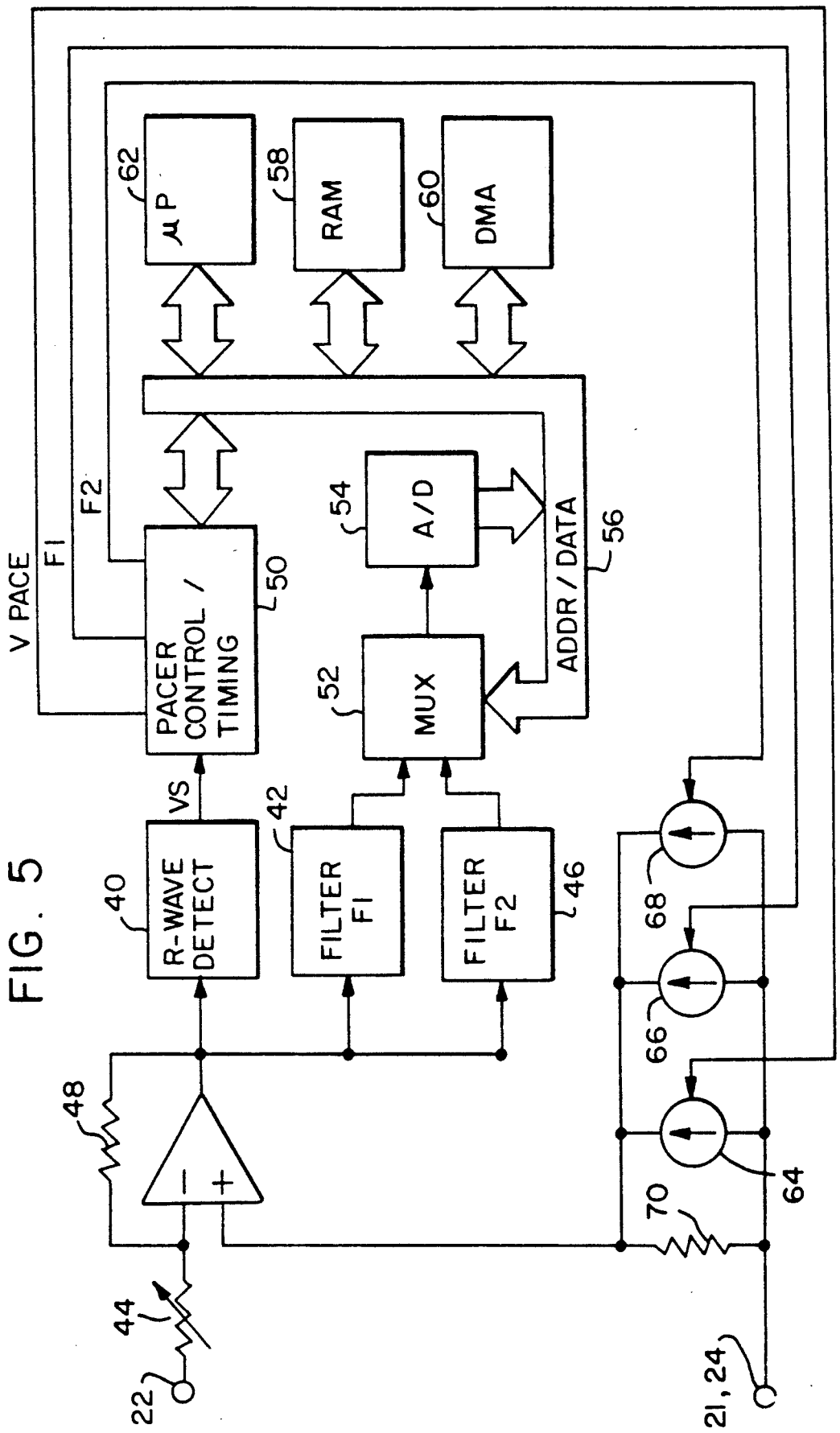
FIG. 5 is a block diagram of a pacemaker employing the present invention.

FIG. 5 is a schematic diagram of an illustrative embodiment of a cardiac pacemaker practicing the present invention. An operational amplifier (op amp) 38 is configured to operate as a field density clamp amplifier as discussed extensively in the above-cited Hudrlik applications. Amplifier 38 has its positive input connected to the reference or case electrode 21 or 24. The negative input to the amplifier 38 is connected to the tip or probe electrode 22. The tip electrode 22 is coupled through a variable resistor 44 which is used to set a virtual load impedance for the system. A feedback path is provided for the amplifier 38 by a resistance 48 which converts current through the virtual load resistor to a proportional voltage.

Operational amplifier 38 maintains its inputs at the same voltage. Therefore, in response to a disturbance in the electrical equilibrium condition at the tissue-electrode interfaces, the amplifier 38 applies current to electrode 22 through virtual load resistor 44 in an amount sufficient to maintain its inputs at equal potentials. As described in the above-cited Hudrlik applications, the current applied to electrode 22 both reflects the power of the passing depolarization wave-front and reestablishes the equilibrium condition at the electrode tissue interface. In operation, the op amp 38 provides a voltage signal at its output which reflects the amount of current applied through virtual load 44 in response to the passage of a cardiac depolarization wave front.

At least in medical applications, it is conventional that input amplifiers have very high input impedances. Ordinary biomedical engineering design practices dictate that a sense amplifier's input impedance must be at least an order of magnitude higher than the source impedance. See for example, "Bioelectric Amplifiers," in *Introduction to Biomedical Equipment Technology* by Carr and Brown, John Wiley & Sons, 1981, pages 41-44 at 42. In accordance with the present invention, however, the input impedance of virtual load resistor 44 to be even less than the source impedance which, in the case of heart tissue, typically is in the range of 500-1000 ohms, resulting in sharply enhanced peaks in the ECG signal Similarly, a low virtual load impedance is also believed beneficial in the present case in which the amplifier is used both to apply the excitation signals and to provide a signal output indicative of tissue impedance.

While the illustrated embodiment employs an operational amplifier 38 to monitor R-waves and to measure the tissue's impedance, other embodiments of the invention may employ other gain cells. While the inventor has employed the particular approach illustrated, it is believed to be within the scope of the invention to employ other circuitry for measurement of the tissue impedance Similarly, it is anticipated that in some embodiments of the invention, separate amplifiers may be employed for R-wave sensing and impedance measurement.

The invention may be practiced with conventional pacing leads and electrodes. However, the operational amplifier circuit illustrated may advantageously be used with electrodes of smaller than conventional surface area, for example as illustrated in FIGS. 4b 4c and 4d. The electrode surface areas of the electrode or electrodes in or on the heart are preferably in the range of 1.0 mm$^2$ squared to 10.0 mm$^2$, for human use. The optimum electrode size will also vary as a function of electrode material, with optimum electrode size generally increasing as the conductivity of the electrode material decreases. For example, the active surface of a vitreous carbon electrode would optimally be somewhat larger than a corresponding platinum electrode. The specific electrode sizes to be employed will vary with application, and should be empirically determined in conjunction with the specific application of the invention.

As described in the above-cited application Ser. No. 07/730,160 by Hudrlik, the operational amplifier 38 may also be used to generate stimulation pulses. In the present case, this is accomplished by means of a controlled signal generator 64 which generates a defined voltage across resistor 70. This voltage, applied to the positive input of operational amplifier 38 results in amplifier 38 delivering current through virtual load resistor 44 in an amount sufficient to maintain the positive and negative inputs of operational amplifier 38 at equal potentials. The current delivered through virtual load resistor 44 serves as a stimulation pulse corresponding to the signal applied to the positive input of amplifier 38. As discussed in the above-cited Hudrlik application, this allows a amplifier 38 to function both as a sense amplifier and an output amplifier, with the amplifier 38 rapidly restoring the electrode/tissue interface to its original equilibrium state following delivery of the stimulation pulse. Signal generator 64 is preferably configured to deliver rectangular pulses of adjustable duration, however, other wave-forms may be employed such as triangular, sinusoidal, or trapezoidal, if desired. One advantage of the use of amplifier 38 to generate the stimulation signal is that it allows generation of stimulation pulses of arbitrary wave-form, constrained only by the output capabilities of the amplifier 38.

Generation of the excitation signals is accomplished in a similar fashion. Signal generators 66 and 68 are adjusted to provide sinusoidal excitation signals at frequencies F-1 and F-2, respectively. Preferably, the excitation signals take the form of sinusoidal signals applied across resistor 70, and to the positive input of amplifier 38. Amplifier 38 will correspondingly provide sinusoidal signals to probe electrode 22 via virtual load resistor 44 in order to maintain its inputs at equal potentials. Preferably the amplitude of the excitation signals applied to the tissue by amplifier 38 is substantially below the threshold for electrical stimulation of the associated tissue. Excitation signals in the range of less than 1 mv to about 100 mv are believed appropriate.

Signal sources 66 and 68 may be activated simultaneously or sequentially. The impedance of the tissue as measured between electrodes 22 and 21/24 will be reflected in the current applied through virtual load resistor 44, thus modulating the amplitude of the output signal from amplifier 38. Thus, the amplitude of the signal output of operational amplifier 38 during application of the drive signals provides a measurement of the impedance of the tissue between the electrodes. It should be understood that in this embodiment, while multiple independent current sources 64,66,68 are illustrated, a single voltage to current converter driven by as summed signals of the selected excitation frequencies would also be workable.

While the inventor has employed the operational amplifier circuit as illustrated to generate pacing and excitation signals, it is anticipated that other embodiments of the invention may employ other voltage or current sources to perform these functions. It is also anticipated that other embodiments of the invention may employ separate current or voltage sources to pace and to generate excitation signals. Similarly, it is anticipated that other embodiments of the invention may employ separate circuits for delivering pacing pulses and for sensing R-waves, as well as separate circuits for delivering excitation signals and for measuring impedance.

The output of operational amplifier 38 is provided to an R-wave detection block 40, a filter 42 tuned to frequency F-1 and a second filter 46 tuned to frequency F-2. The output of R-wave detection circuit 40 is coupled to pacer control/timing circuitry 50, which performs all timing and control functions necessary for both cardiac pacing and for activation and control of the various signal generators 64, 66 and 68. The outputs of filters 42 and 46 are provided to a multiplexor 52, and thereafter to an analog to digital converter 54 so that the resulting signals may be digitized for storage and analysis. Overall control of the operation of the pacemaker is provided by microprocessor 62, under control of stored programming in random access memory 58. Entry of programming information into random access memory 58 and readout of memory stored in random access memory 58 is accomplished by direct memory addressing 60, which allows data storage even while microprocessor 62 is in a quiescent state.

Operation of the pacemaker is best understood by beginning with the sensing of a depolarization of the ventricle in which electrode 22 is located. The resulting disturbance in the electrode-tissue equilibrium condition at electrode 22 results in delivery of current by amplifier 38 through virtual load resistor 44 in order to maintain the inputs of the amplifier at equal potentials. The output of amplifier 38 is coupled to R-wave detector 40, which compares its output amplitude to a predetermined sensing threshold. R-wave detection circuitry 40 may correspond to any known R-wave detection circuitry, and is a conventional portion of most cardiac pacemakers. The threshold to which the output of amplifier 38 is compared may be fixed or may vary depending upon the detected amplitude of previous R-waves. In any case, a digital signal (VS) is provided by R-wave detector 40 to pacer control/timing logic 50.

Pacer control/timing logic 50 includes the basic timers which control operation of the pacemaker. In particular, it includes at least one programmable timer into which microprocessor 62 may load predetermined time intervals and also includes the decoding logic associated with the timer for decoding the expiration of various predetermined time intervals following resetting of the timer. Alternatively, pacer control/timing logic 50 may include separate timers, each individually controllable, for defining the various time intervals necessary for implementation of cardiac pacing functions. At the very least, pacer control/timing circuitry 50 should be capable of providing an escape interval, indicative of the interval between adjacent pacing pulses and the interval separating a sensed depolarization from the subsequent pacing pulse, a blanking period associated with the delivery of a stimulation pulse, during which the output of R-wave detector 40 is not considered, and one or more time intervals controlling activation of signal sources F-1 and F-2 to delivery excitation signals via amplifier 38.

In response to the detection of a depolarization by R-wave detector 40, or delivery of a pacing pulse, pacer control/timing circuitry 50 generates an interrupt on an address/data bus 56, which awakens microprocessor 62, which in turn calculates appropriate values for the next subsequent pacing interval, and loads it into pacer control/timing circuitry via address/data bus 56.

To obtain impedance information, following detection of a depolarization or the delivery of a pacing pulse, pacer control/timing circuitry also generates signals on lines 74 and 76 for activation of signal sources 66 and 68. Signal sources 66 and 68 may be activated sequentially or simultaneously and preferably generate signals at frequencies F-1 and F-2, as discussed above. During application of the excitation signals, the output of amplifier 38 is applied to the inputs of filters 42 and 46. Filters 42 and 46 are band pass filters having center frequencies tuned to F-1 and F-2 respectively. Their outputs are applied to multiplexor 52, under control of microprocessor 62, and are digitized by analog/digital converter 54. The digitized signals may be stored in random access memory 58 under control of direct memory addressing circuitry 60.

If the device is intended to measure the impedance of heart tissue and/or blood during depolarization or repolarization, measurement will be initiated immediately or soon after delivery of a pacing pulse or sensing of a ventricular depolarization. Similarly, if respiration is to be measured, impedance measurements may be taken at this time.

In the event that a more complete record of the impedance changes associated with a depolarization is desired, impedance measurements may be taken continuously, except for a time interval associated with the delivery of a pacing pulse. The measured impedance values may be stored in a looping memory of the type in which the most recent data is written over the oldest data, preferably with the capacity to store at least 200 ms. of measurements. Upon detection of the occurrence of a spontaneous depolarization, either by analysis of the impedance measurements or by means of a conventional R-wave detector, a time delay of 100 ms or greater may be specified, with the memory frozen after this time interval, analogous to the system disclosed in U.S. Pat. No. 4,223,678, issued to Langer et al. and incorporated by reference in its entirety. The data available for analysis would include impedance measurements before, during and after the depolarization.

If the device is intended to measure the condition of the tissue beginning prior to depolarization, the expected time of the next depolarization may be calculated and the signal sources 66 and 68 may be activated just prior to the expected depolarization to yield information on passive tissue conductance properties. The device may alternately activate the signal sources 66,68 during the period between depolarizations, to provide baseline data which could be compared to the impedance changes associated with depolarizations and used to quantify or identify ischemia.

As illustrated, the outputs of filters 42 and 46 are applied directly to multiplexor 52. However, in some embodiments it may be desirable to pass the outputs of filters 42 and 46 through low-pass filters to strip off the carrier frequencies F-1 and F-2, performing an envelope demodulation of the band pass filters, outputs for presentation to multiplexor 52. In either case, the filter outputs are stored in random access memory 58 and analyzed under control of microprocessor 62 to measure the relative impedance at the two selected frequencies.

As discussed above, the measured impedance values may be employed to detect changes in tissue condition, such as those induced by ischemia and by drug therapies, allograft rejection and lead fractures or insulation degradation. For example, in the context of cardiac pacemaker, microprocessor 62 may average the stored impedance valves at the two frequencies over a period of hours, days, weeks, or even months, compare the measured impedances at the two frequencies, and in response to detection of a predefined change in the relationship of the relative average impedance values over these extended time periods, may provide an increase in minimum or base pacing rate in an attempt to counteract the detected ischemia.

Alternatively, in the event that the reflected change in relative measured impedances of the two frequencies reflects a variation in tissue condition as a function of an applied drug therapy, the microprocessor 62 may set an internal flag for external telemetry to notify the physician at a later date. Additionally, although not illustrated herein, it is contemplated that the pacemaker may provide an informational signal to an associated implanted drug dispenser, allowing for modulation of the drug therapy in response to detected changes in tissue impedance.

In the event that the impedance measurement system is employed to measure respiration for control of pacing rate, it is envisioned that electrode 22, located within the right ventricle and the can electrode 24 of the pacemaker will preferentially be used, to allow for a substantial volume of lung tissue to be located within the sensing field of the electrodes. In such case, microprocessor 62 will similarly control processing of the outputs of filters 42 and 46, however, the time scale employed will be significantly shorter. For example, the measured differential between the output of filter 42, centered at the selected local impedance maximum and filter 46, selected for a local impedance minimum will both be processed to determine their amplitudes over much shorter time periods. For example, the amplitude of the output of filter F-2 may be subtracted from the amplitude of the output of filter F-1 to derive a measurement of instantaneous, frequency dependant impedance characteristics. The modulation of the instantaneous impedance characteristics may be measured, and the amplitude and rate of modulation of the frequency dependant impedance characteristics may used to calculate respiration rate and/or minute volume, in a manner analogous to that described in the above-cited Plicchi, Nappholtz and Alt patents.

For example, the signal indicative of the instantaneous impedance difference at the two excitation frequencies may be applied to a delta modulator, and the measurement to measurement change in measured instantaneous impedance difference may be summed over a short period of time, for example 30 seconds, to derive a measurement of minute ventilation. As noted above, this approach should provide a self referencing measurement system for the particular individual in whom the device is implanted. Alternatively, any of the signal processing techniques employed by the above-cited Alt, Plicchi and Nappholtz patents may be employed in order to derive a measurement of respiration and/or minute volume form individual measurements of instantaneous impedance difference at the two excitation frequencies.

FIG. 6 illustrates an alternative embodiment of the present invention, employing a somewhat different impedance measurement system. System components which are identical to those illustrated in FIG. 5 are labelled with the same numbers as used in FIG. 5. Only the additional or alternative structures are discussed in detail below.

In FIG. 6, a pink noise generator 80 is substituted for signal sources 66 and 68 in FIG. 5. Similarly, tunable band pass filers 82 and 84 are substituted for fixed band pass filers 42 and 46 in FIG. 5. Control of the band pass characteristics of filters 82 and 84 is provided by microprocessor 162 via address/data buss 56. In a system such as illustrated, it is contemplated that the selection of the frequencies of tunable band pass filters 82 and 84 will be accomplished in response to an initial scan through the frequency range provided by pink noise generator 80. In response to such a scan, as discussed above in conjunction with FIG. 3, frequencies indicative of local impedance maxima and minima may be identified, and used to specifically select the center frequencies of filters 82 and 84. Thereafter operation of the device may correspond to that of the device illustrated in FIG. 4, with the exception that rather than sequentially or simultaneously activating two separate signal sources to excite the tissue to be measured, pink noise generator 80 would instead by activated.

In a first embodiment, the outputs of tunable filters 82 and 84 may be stored in random access memory 58 and analyzed by microprocessor 62 to determine whether a shift in local minima and maxima has occurred, as discussed above. The occurrence of a shift in frequency dependent impedance characteristics may trigger a change the base pacing, or other corrective action may be taken as described in conjunction with FIG. 5. In this case, the corrective (increased pacing rate or alteration of drug regimen) would be directed toward restoring the original frequency dependent impedance characteristics of the tissue, as indicative of a return to normal tissue condition. Upon detection of a return to normal condition, variation in the pacing or drug therapy would be discontinued pending detection of a subsequent change in frequency dependant tissue impedance.

In a second embodiment, it is envisioned that in response to detection of a change in the frequency dependant impedance of the tissue, a new scan through the frequencies associated with pink noise generator 80 may be undertaken under control of microprocessor 62, by varying the center frequencies of tunable band pass filters 82 and 84. In such case, a measurement of the frequency shift of local impedance minima and maxima may provide useful additional diagnostic information.

The invention as disclosed in FIGS. 5 and 6 will be understood to be implemented in a multi-programmable, multi-mode, processor based system of the type described in Medtronic U.S. Pat. No. 4,754,753 for example, and the various timing intervals and signal processing to be described may be effected by the processor under software algorithm control. Although these exemplary embodiments of the present invention have been shown and described, it will be apparent to those having ordinary skill in the art that a number of changes, modifications, or alterations to the invention as described herein may be made, none of which depart form the spirit of the present invention. For example, substitution of other circuit architectures, such as dedicated function digital or analog circuitry for the microprocessor based system illustrated is believed within the capabilities of those of skill in the art. It is also envisioned that the diagnostic value of the impedance related information generated by the present invention will have broad applicability. Therefore use of the impedance measurements to affect other types of therapies than those disclosed is believed likely as the benefit of the invention becomes widely understood. All such changes, modifications and alterations should therefore be seen within the scope of the present invention.

In conjunction with the above disclosure, I claim:

1. A cardiac pacemaker, comprising:
   pulse generator means for generating cardiac pacing pulses and for delivering said cardiac pacing pulses to a patient's heart;
   timing means coupled to said pulse generator means for controlling the rate at which said pacing pulses are generated;
   means for monitoring said patient's body tissue, said means for monitoring comprising a pair of electrodes adapted to be in contact with said tissue to be monitored, signal generator means for generating electrical signals at at least first and second frequencies for application to said pair of electrodes, measuring means responsive to signals at said first and second frequencies, for measuring the impedance between said pair of electrodes at said first and second frequencies, and means for detecting changes in the relationship of said measured impedances at said first and second frequencies; and
   means coupled to said monitoring means and to said timing means for varying the rate at which said pacing pulses are generated in response to the detection of changes in said relationship of said impedances measured at said first and second frequencies.

2. A pacemaker according to claim 1 wherein aid first and second frequencies are separated by a factor of ten or greater.

3. A pacemaker according to claim 1 wherein said pacemaker further comprises means for activation of said monitoring means at predetermined times following generation of said pacing paces.

4. A pacemaker according to claim 1 wherein said signal generator means comprises first and second signal sources each functioning to generate one of said first and second frequencies.

5. A pacemaker according to claim 1 wherein said signal generator means comprises a pink noise generator, for generating electrical signals across a band of frequencies including said first and second frequencies.

6. A pacemaker according to claim 1 or claim 4 or claim 5 wherein said pacemaker further comprises first and second tuned band-pass filter means for selectively allowing passage of signals at said first and second frequencies and wherein said measuring means comprises mean responsive to said first and second band-pass filter means.

7. A pacemaker according to claim 1 wherein said monitoring means comprises means for calculating average values of said impedances measured at said first and second frequencies over predetermined periods of time and wherein said detecting means comprises mean for comparing said average values to detect changes in said relationship of said measured impedances at said first and second frequencies.

8. A pacemaker according to claim 1 wherein said monitoring means comprises means for measuring variations in said impedances at said first and second frequencies associated with functioning of said body tissue wherein said detecting means comprises means for detecting changes in said variations over time.

9. A pacemaker according to claim 1 wherein said pair of electrodes are adapted for location such that a substantial amount of said patient's lung tissue is between said electrodes and wherein said monitoring means comprises means for measuring the modulation of said relationship of said impedances measured at said first and second frequencies and wherein said varying means comprises means for varying the rate of generation of said pacing pulses as a function of the rate of said measured modulation.

10. A pacemaker according to claim 1 wherein said pair of electrodes are adapted for location such that at least one of said pair of electrodes is adapted for location adjacent heart tissue and wherein said monitoring means comprises means for measuring changes in said relationship of said impedances measured at said first and second frequencies and wherein said varying means comprises means for varying the rate of generation of said pacing pulses in response to said measured changes.

11. A pacemaker according to claim 1 wherein said pair of electrodes are adapted for location such that at least one of said pair of electrodes is adapted for location adjacent heart tissue and wherein aid pulse generator means is coupled to aid at least one of said pair of electrodes.

12. A physiological monitoring device, comprising:
   means for monitoring the condition of a patient's body tissue, said means for monitoring comprising a pair of electrodes adapted to be in contact with said tissue to be monitored, signal generator means for generating electrical signals at at least first and second frequencies for application to said pair of electrodes, measuring means responsive to signals at said first and second frequencies, for measuring the impedance between said pair of electrodes at said first and second frequencies, and means for detecting changes in the relationship of said measured impedances at said first and second frequencies, wherein said monitoring means comprises mean for calculating average values of said impedances measured at said first and second frequencies over predetermined periods of time and wherein said detecting means comprises means for comparing said average values to detect changes in said relationship of said measured impedances at said first and second frequencies; and means coupled to said monitoring means for providing indications of said detected changes in said relationship of said impedances measured at said first and second frequencies.

13. A device according to claim 12 wherein said first and second frequencies are separated by a factor of ten or greater.

14. A device according to claim 12 wherein said signal generator means comprises first and second signal sources each functioning to generate one of said first and second frequencies.

15. A device according to claim 12 wherein said signal generator means comprises means for generating electrical signals across a band of frequencies including said first and second frequencies.

16. A device according to claim 12 or claim 14 or claim 15 wherein said device further comprises first and second tuned band-pass filter means for selectively allowing passage of signals at said first and second frequencies and wherein said measuring means comprises means responsive to said first and second band-pass filter means.

17. A device according to claim 12 wherein said pair of electrodes are adapted for location such that a substantial amount of said patient's lung tissue is between said electrodes and wherein said monitoring means comprises means for measuring the modulation of said relationship of said impedances measured at said first and second frequencies.

18. A device according to claim 12 wherein said pair of electrodes are adapted for location such that at least one of said pair of electrodes is adapted for location adjacent heart tissue.

19. A method of monitoring the condition of a patient's tissue, comprising:

determining a first frequency at which said tissue displays an impedance minimum and a second frequency at which said tissue displays an impedance maximum;

locating a pair of electrodes in contact with said tissue;

applying electrical signals at said first and second frequencies to said pair of electrodes;

measuring the impedance between said pair of electrodes at said first and second frequencies; and measuring changes in the relationship of said measured impedances at said first an second frequencies.

20. A method according to claim 19 wherein said change measuring step comprises calculating average values of said impedances measured at said first and second frequencies over predetermined periods of time comparing said average values to detect changes in said relationship of said measured impedances at said first and second frequencies.

21. A method according to claim 19 wherein said step of applying electrical signals comprises applying electrical signals across a band of frequencies including said first and second frequencies.

22. A method according to claim 19 wherein said locating step comprises locating said pair of electrodes such hat a substantial amount of said patient's lung tissue is between said pair of electrodes.

23. A method according to claim 19 wherein said locating step comprises locating at least one of said pair of electrodes adjacent heart tissue.

* * * * *